United States Patent
Hill (10) Patent No.: US 11,992,638 B2
(45) Date of Patent: May 28, 2024

(54) SYSTEM AND METHOD FOR PATIENT SKIN TREATMENT AND IRRIGATION

(71) Applicant: AZ Solutions LLC, Bloomfield Hills, MI (US)

(72) Inventor: Derek Hill, Bloomfield Hills, MI (US)

(73) Assignee: AZ SOLUTIONS LLC, Bloomfiled Hills, MI (US)

( * ) Notice: Subject to any disclaimer, the term of this patent is extended or adjusted under 35 U.S.C. 154(b) by 627 days.

(21) Appl. No.: 17/186,433

(22) Filed: Feb. 26, 2021

(65) Prior Publication Data
US 2021/0178052 A1    Jun. 17, 2021

Related U.S. Application Data (63) Continuation of application No. 15/686,612, filed on Aug. 25, 2017, now Pat. No. 10,960,129.

(51) Int. Cl.
*A61M 3/02*    (2006.01)
*A61K 33/30*    (2006.01)
(Continued)

(52) U.S. Cl.
CPC ........... *A61M 3/0279* (2013.01); *A61K 33/30* (2013.01); *A61M 1/77* (2021.05); *A61M 3/005* (2013.01);
(Continued)

(58) Field of Classification Search
CPC .. A61M 3/0233; A61M 1/774; A61M 3/0279; A61M 1/77; A61M 3/005;
(Continued)

(56) References Cited

U.S. PATENT DOCUMENTS

| | | | |
|---|---|---|---|
| 4,540,403 | A | 9/1985 | Theeuwes |
| 4,786,279 | A | 11/1988 | Wilkinson et al. |

(Continued)

FOREIGN PATENT DOCUMENTS

| | | |
|---|---|---|
| CN | 1248155 A | 3/2000 |
| CN | 104826114 A | 8/2015 |

(Continued)

OTHER PUBLICATIONS

First Indian Office Action dated Sep. 9, 2021 for Indian Application No. 202017012635, received in related application.
(Continued)

*Primary Examiner* — Susan S Su
(74) *Attorney, Agent, or Firm* — BROOKS KUSHMAN P.C.

(57) ABSTRACT

A system for irrigating a patient's skin. The system includes a fluid container that includes a first compartment and a second compartment, the first compartment being adapted to retain a first fluid on a first side of a divider and the second compartment being adapted to retain a second fluid on a second side of the divider. The system also includes an irrigation sleeve adapted cover a portion of the patient's skin. The system also includes a fluid charging portion adapted to receive a portion of the first fluid and a portion of the second fluid, wherein the portion of the first fluid reacts with the portion of the second fluid to form a charged compound in the fluid charging portion. The system also includes a compound delivery portion that extends at a first end of the compound delivery portion from the fluid charging portion, the compound delivery portion being adapted to deliver the charged compound from the fluid charging portion to the irrigation sleeve.

8 Claims, 5 Drawing Sheets

(51) Int. Cl.
  *A61M 1/00* (2006.01)
  *A61M 3/00* (2006.01)
  *A61M 35/00* (2006.01)
  A61M 39/22 (2006.01)

(52) U.S. Cl.
  CPC .......... *A61M 3/0233* (2013.01); *A61M 35/00* (2013.01); *A61M 35/003* (2013.01); *A61M 39/22* (2013.01); *A61M 2205/583* (2013.01); *A61M 2205/7545* (2013.01); *A61M 2210/086* (2013.01)

(58) Field of Classification Search
  CPC .... A61M 35/00; A61M 35/003; A61M 39/22; A61M 2205/583; A61M 2205/7545; A61M 2210/086; A61K 33/30
  See application file for complete search history.

(56) References Cited

U.S. PATENT DOCUMENTS

| | | | |
|---|---|---|---|
| 4,894,061 A * | 1/1990 | Dobruskin | A61M 3/0279 215/12.2 |
| 5,059,187 A | 10/1991 | Sperry et al. | |
| 5,125,837 A | 6/1992 | Warrin | |
| 5,152,461 A | 10/1992 | Proctor | |
| 5,227,168 A | 7/1993 | Chvapil et al. | |
| 5,411,176 A | 5/1995 | Favre | |
| 5,753,217 A | 5/1998 | Christopfel | |
| 5,830,197 A | 11/1998 | Rucinski | |
| 5,908,865 A | 6/1999 | Doe et al. | |
| 6,283,936 B1 | 9/2001 | Tavger | |
| 6,319,243 B1 | 11/2001 | Becker et al. | |
| 6,409,992 B1 | 6/2002 | Kleinberg et al. | |
| 6,423,300 B1 | 6/2002 | Kleinberg et al. | |
| 6,558,710 B1 | 5/2003 | Godfrey | |
| 6,635,035 B1 | 10/2003 | Marasco | |
| 6,929,790 B2 | 8/2005 | Kleinberg et al. | |
| 6,946,142 B2 | 9/2005 | Chang | |
| 7,959,617 B2 | 6/2011 | Rucinski | |
| 8,562,907 B2 | 10/2013 | Green | |
| 9,044,466 B2 | 6/2015 | Cohen et al. | |
| 9,433,711 B2 | 9/2016 | Pratt et al. | |
| 9,549,878 B2 | 1/2017 | Le Ouay et al. | |
| 9,556,471 B2 | 1/2017 | LeJuene | |
| 10,137,467 B2 | 11/2018 | Alluigi | |
| 2002/0068913 A1 | 6/2002 | Fleischmann | |
| 2002/0074347 A1 | 6/2002 | Murry et al. | |
| 2004/0063600 A1 | 4/2004 | Williams et al. | |
| 2005/0035153 A1 | 2/2005 | Brown | |
| 2005/0192546 A1 | 9/2005 | Griego | |
| 2006/0155260 A1 | 7/2006 | Blott et al. | |
| 2007/0029275 A1 | 2/2007 | Hantman et al. | |
| 2007/0141128 A1 | 6/2007 | Blott | |
| 2007/0225662 A1 | 9/2007 | Rucinski | |
| 2007/0225663 A1 | 9/2007 | Watt et al. | |
| 2007/0237810 A1 | 10/2007 | Wellinghoff | |
| 2011/0054283 A1 | 3/2011 | Shuler | |
| 2011/0097372 A1 | 4/2011 | Rucinski | |
| 2012/0035559 A1 | 2/2012 | Rucinski | |
| 2012/0302973 A1 | 11/2012 | Locke | |
| 2013/0164358 A1 | 6/2013 | Cohen et al. | |
| 2013/0165821 A1 | 6/2013 | Freedman et al. | |
| 2013/0178785 A1 | 7/2013 | Papay | |
| 2013/0270490 A1 | 10/2013 | De La Vega | |
| 2014/0213990 A1 | 7/2014 | Gorinshteyn | |
| 2014/0263448 A1 | 9/2014 | Erskine-Smith | |
| 2014/0276288 A1 | 9/2014 | Randolph et al. | |
| 2014/0364818 A1 | 12/2014 | Vogt | |
| 2015/0216765 A1 | 8/2015 | Le Ouay | |
| 2015/0232260 A1 | 8/2015 | Dann et al. | |
| 2015/0258257 A1 | 9/2015 | Kidman | |
| 2015/0298149 A1 | 10/2015 | Alluigi | |
| 2016/0000088 A1 | 1/2016 | Nakamura | |
| 2016/0136350 A1 | 5/2016 | Yoo | |
| 2016/0235692 A1 | 8/2016 | Rucinski | |
| 2016/0325028 A1 | 11/2016 | Locke et al. | |
| 2017/0028144 A1 | 2/2017 | Flickinger | |
| 2017/0080219 A1 | 3/2017 | Balsamo | |
| 2017/0100338 A1 | 4/2017 | Awad | |
| 2017/0121098 A1 | 5/2017 | Kaiser et al. | |
| 2017/0216852 A1 | 8/2017 | Gopalan et al. | |
| 2017/0239455 A1 | 8/2017 | Richards | |
| 2019/0322442 A1 | 10/2019 | Thomsen | |
| 2020/0039732 A1 | 2/2020 | Ditto et al. | |

FOREIGN PATENT DOCUMENTS

| | | |
|---|---|---|
| CN | 106687218 A | 5/2017 |
| JP | 2002524212 A | 8/2002 |
| JP | 2015147766 A | 8/2015 |
| WO | 2005030297 A1 | 4/2005 |
| WO | 2005046761 A | 5/2005 |
| WO | 2011/130246 A2 | 10/2011 |

OTHER PUBLICATIONS

European Office Action dated Mar. 22, 2023 which issued in related EP Application No. 18 847 925.7. 6 pages.

Japanese Office Action dated Sep. 8, 2022 for JP Application No. 20205322868 which issued in related application. English translation provided.

NPL_First Office Action dated Sep. 4, 2023 for Chinese Application No. CN 201880055296.3 which issued in a related application. 10 pages.

International Search Report for PCT/US18/48149, dated Oct. 5, 2018.

C. Wu et al., "Zinc as an agent for the prevention of biofilm formation by pathogenic bacteria," Journal of Applied Microbiology, vol. 115, pp. 30-40, 2013.

S.C. Fu, et al., "Development of vitamin C irrigation saline to promote graft healing in anterior cruciate ligament reconstruction," Journal of Orthopaedic Translation, vol. 1, pp. 67-77, 2013.

Z. Tang, et al., "Design and characterizations of novel biodegradable Zn—Cu—Mg alloys for potential biodegradable implants," Materials and Design, vol. 117, pp. 84-94, 2017.

J. Niu, et al., "Research on a Zn—Cu alloy as a biodegradable material for potential vascular stents application," Materials Science and Engineering C., vol. 69, pp. 407-413, 2016.

L.K. Hung, et al., Local Vitamin-C Injection Reduced Tendon Adhesion in a Chicken Model of Flexor Digitorum Profundus Tendon Inquiry, The Journal of Bone and Joint Surgery, vol. 95:e41, pp. 1-7, 2013.

International Search Report for PCT/US2018/048149, dated Apr. 20, 2021.

Australian Office Action dated Jun. 30, 2023 which issued in related AU Application No. 2018321929. 3 pages.

U.S. Final Office Action dated Jul. 21, 2023 which issued in related U.S. Appl. No. 16/641,749. 22 pages.

* cited by examiner

SYSTEM AND METHOD FOR PATIENT SKIN TREATMENT AND IRRIGATION

CROSS REFERENCE TO RELATED APPLICATIONS

This application is a continuation of U.S. application Ser. No. 15/686,612, filed Aug. 25, 2017, (pending), the disclosure of which is incorporated in its entirety by reference herein.

TECHNICAL FIELD

This disclosure relates to a system and method treating a patient, and in particular, to treating and irrigating a patient's skin.

BACKGROUND

Surgical wounds or chronically occurring wounds, such as diabetic or vascular foot or leg ulcers, can become inoculated during surgery or infected with bacteria or other infectious organisms. Prophylaxis to prevent and/or cure infections can be provided by eradicating inoculation, colonization or contamination. Further, prevention of infection, inoculation or colonization of surgical wounds or chronically occurring wounds can be provided by a lasting antimicrobial activity in a nontoxic irrigant which offers persistent antimicrobial activity. This can be accomplished if the irrigant is allowed to remain in or around the wound, eliciting persistent antimicrobial activity.

Increasing metabolism and growth of anaerobic bacteria in such wounds may increase when an oxidation-reduction potential ($E_h$) is decreased. The $E_h$ in such wound areas can decrease, for example, when oxygen in the wound area is decreased and may decrease responsive to other changes in the characteristics of the wound area. Conversely, by increasing the $E_h$ in a wound area, metabolism and growth of anaerobic bacteria may be decreased, which may prevent and/or cure an infection in a wound area. Increasing the $E_h$ in a wound area may include irrigating the wound area with one or more ion rich compounds, such as a charged zinc compound having free available zinc ions and at least one $E_h$ raising component.

SUMMARY

Disclosed herein are implementations of aspects, features, elements, implementations, and embodiments of irrigating a patient's wounds.

An aspect of the disclosed embodiments is a system for irrigating a patient's skin. The system includes a fluid container that includes a first compartment and a second compartment, the first compartment being adapted to retain a first fluid on a first side of a divider and the second compartment being adapted to retain a second fluid on a second side of the divider. The system also includes an irrigation sleeve adapted to cover a portion of the patient's skin. The system also includes a fluid charging portion adapted to receive a portion of the first fluid and a portion of the second fluid, wherein the portion of the first fluid reacts with the portion of the second fluid to form a charged compound in the fluid charging portion. The system also includes a compound delivery portion that extends at a first end of the compound delivery portion from the fluid charging portion, the compound delivery portion being adapted to deliver the charged compound from the fluid charging portion to the irrigation sleeve.

Another aspect of the disclosed embodiments is a method for irrigating a patient's skin. The method includes: retaining a first fluid on a first side of a divider; retaining a second fluid on a second side of a divider, the second side of the divider being disposed opposite the first side of the divider; covering a portion of the patient's skin with an irrigation sleeve; receiving a portion of the first fluid and a portion of the second fluid, wherein the portion of the first fluid reacts with the portion of the second fluid to form a charged compound; and delivering the charged compound from a fluid charging portion to the irrigation sleeve.

Another aspect of the disclosed embodiments is a system for irrigating a patient's skin. The system includes an irrigation sleeve adapted to cover a portion of the patient's skin. The system also includes a fluid charging portion adapted to receive a portion of a first fluid and a portion of a second fluid, wherein the portion of the first fluid reacts with the portion of the second fluid to form a charged compound in the fluid charging portion. The system also includes a compound delivery portion adapted to deliver the charged compound from the fluid charging portion to the irrigation sleeve while the charged compound is charged.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Surgical wounds or chronically occurring wounds, such as diabetic foot or leg ulcers, can become infected with bacteria or other infectious organisms. Prophylaxis to prevent and/or solutions to cure infections can be provided by preventing inoculation or contamination. Further, prevention or treatment of infection, inoculation, or colonization of surgical wounds or chronically occurring wounds can be provided by a lasting antimicrobial activity in a nontoxic irrigant which offers persistent antimicrobial activity. This can be accomplished if the irrigant is allowed to remain in or around the wound, eliciting persistent antimicrobial activity.

Metabolism and growth of anaerobic bacteria in such wounds may increase when an oxidation-reduction potential ($E_h$) is decreased. The $E_h$ in such wound areas can decrease, for example, when oxygen in the wound area is decreased or in response to other changes in the characteristics of the wound area. Conversely, by increasing the $E_h$ in a wound area, metabolism and growth of anaerobic bacteria may be decreased, which may prevent and/or cure an infection in a wound area. Increasing the $E_h$ in a wound area may include irrigating the wound area with one or more electron-rich or ion-rich compounds, such as a charged zinc compound having free available zinc ions and at least one $E_h$ raising component. Accordingly, a system that charges a charged compound and provides the charged compound to a wound area and/or the patient's skin is desirable.

In some embodiments, according to the principles of the present disclosure, an ion-rich or electron-rich compound suitable for treating such wound areas can be formed by combining a first fluid and a second fluid in a charging area. For example, in some embodiments, a system for irrigating a patient's skin can include a fluid container, such as an intravenous bag or bags hung from an intravenous stand. The fluid container includes a first fluid compartment and a second fluid compartment, or the two fluids could be held in separate containers. In some embodiments, a first fluid, such as zinc chloride ($ZnCl_2$), is retained in the first fluid compartment and a second fluid, such as sodium chlorite ($NaClO_2$), is retained in the second fluid compartment. Before irrigating the patient's skin, a portion of the first fluid and a portion of the second fluid is released from the first fluid compartment and the second fluid compartment, respectively, into a fluid charging portion. The portion of the first fluid and the portion of the second fluid mix and/or interact in the fluid charging portion to form a charged compound. For example, a portion of the $ZnCl_2$ interacts with a portion of the $NaClO_2$ to form a charged zinc compound having free available zinc ions and at least one $E_h$ raising component (e.g., the $NaClO_2$ acts like an $E_h$ raising component when interacting with the $ZnCl_2$). By providing the charged compound to a wound area, the free available zinc ions and the at least one $E_h$ raising component have been shown to prevent lowering of the $E_h$ levels in the wound area, thereby inhibiting metabolism and/or growth of anaerobic bacteria, which may prevent and/or cure infections in the wound area.

The system may include an irrigator. For example, the system may include an irrigation sleeve, an aerosol irrigator, or other suitable irrigator. The charged compound may be delivered to the irrigator from the fluid charging portion. The irrigator can then be used to apply the charged compound to a patient's skin. For example, the irrigator can be used by a medical professional to apply the charged compound to a chronically occurring wound, to an operative and/or post-operative surgical wound, to an injury wound, directly to an area on the patient's skin that does not include a wound, to other suitable areas on the patient's skin, or a combination thereof. Chronically occurring wounds may include diabetes ulcers, decubitus ulcers, venous stasis ulcers, skin affected by eczema, skin affected by psoriasis, chronic skin infections, other suitable chronically occurring wounds, or a combination thereof. In some embodiments, the charged compound may be applied to non-chronically occurring wounds, such as, skin affected by contact with poison ivy, poison oak, skin affected by other skin irritants, skin affected by allergic reactions, or other suitable non-chronically occurring wounds, or a combination thereof.

In some embodiments, the system is adapted to prevent irrigation of the patient's skin and/or wound area when the charged compound is not charged. For example, after a period of time, the charged compound may lose its charge, such that, an amount of free available zinc ions in the charged compound may be reduced, which may render the charged compound ineffective for preventing the lowering of $E_h$ in a wound area. Additionally, or alternatively, as the charged compound loses its charge, the charged compound may become hazardous to the patient. For example, as the charged compound loses its charge, the metabolism and/or growth of anaerobic bacteria may be promoted.

In some embodiments, the system may include a valve disposed at or near the fluid charging portion. The valve may be manually or automatically controlled and may control flow of the charged compound to the irrigator. For example, a medical professional operating the system may open the valve to release the charged compound from the fluid charging portion. The medical professional may then close the valve after a predetermined time and/or after a predetermined amount of the charged compound has been released from the fluid charging portion. The predetermined amount of time and/or the predetermined amount of charged compound may correspond to an amount of charged compound that the irrigator can apply to the wound area and/or the patient's skin before the charged compound loses its charge.

In some embodiments, the system may include a timer, such as a stopwatch, a counter, a clock, or other suitable time. The timer may be disposed on a portion of the system that is readily visible to the medical professional operating the system. For example, the time may be disposed at or near the container, at or near the irrigator, or other suitable position on the system. The timer may act as a visual guide for the operator to determine when the charged compound has lost or started to lose its charge. The medical professional may stop irrigating the wound area and/or patient's skin based on the time. In some embodiments, the time may include a countdown time. For example, the timer may be started when charged compound is released from the fluid charging portion. The timer may be set to an amount of time that the charged compound will retain enough free available zinc ions to effectively increase $E_h$ in the wound area. The medical professional may stop irrigating the wound area and/or patient's skin when the timer reaches zero.

Figure 1:
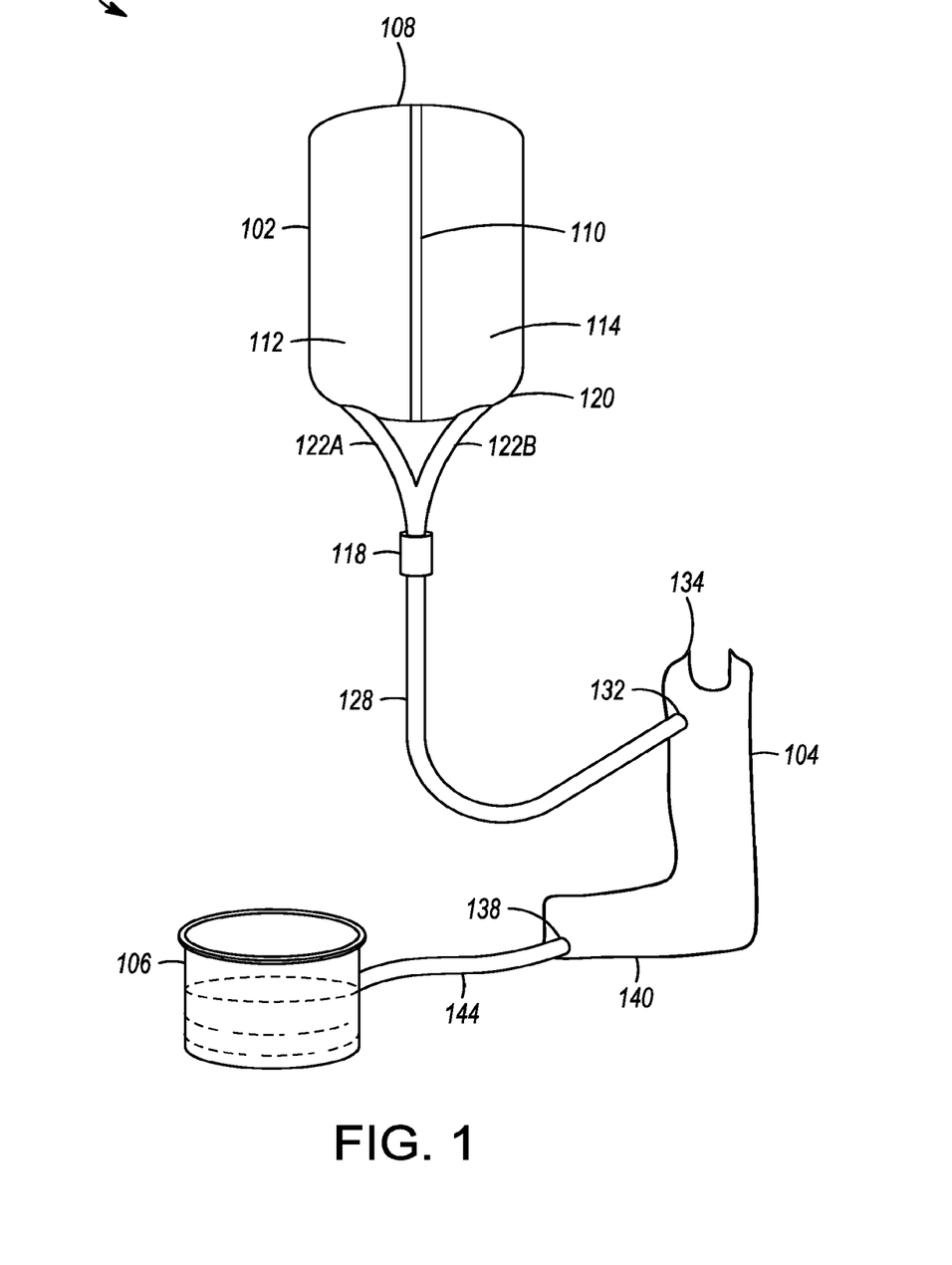
FIGS. 1 and 2 generally illustrate a wound and/or skin irrigation system according to the principles of the present disclosure.
Figure 2:
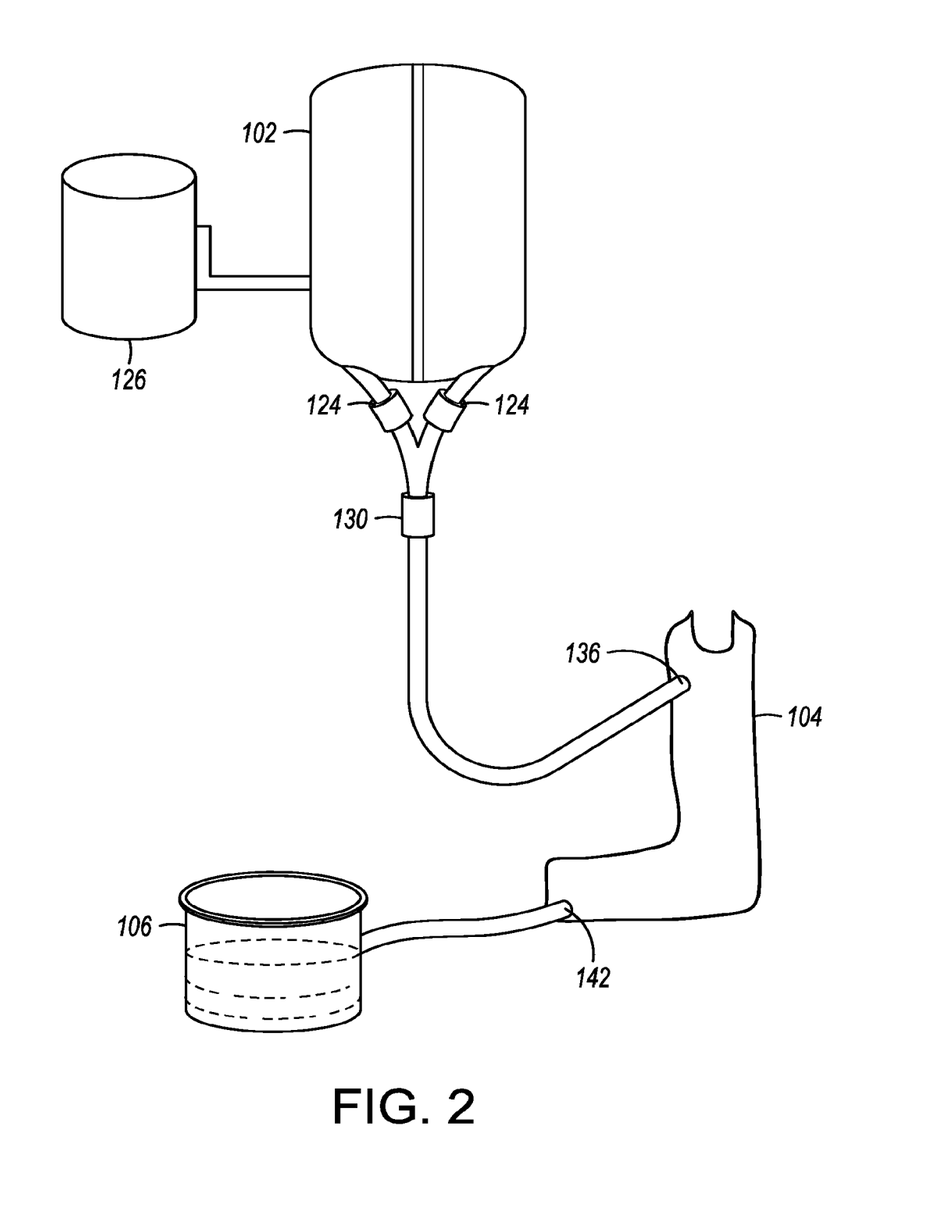

FIGS. 1 and 2 generally illustrate a patient wound and/or skin irrigation system 100, according to the principles of the present disclosure. The system includes a container 102, an irrigator or irrigation sleeve 104, and a reservoir 106. In some embodiments, the container 102 includes an intravenous bag, a canister having cylindrical profile or other suitable profile, or other suitable container. The container 102 is adapted to receive one or more fluids. For example, the container 102 includes a first or upper portion 108. The upper portion 108 may include an opening and/or a port adapted to receive the one or more fluids. In some embodiments, the upper portion 108 includes a plurality of openings and/or ports adapted to receive fluid.

In some embodiments, the container 102 includes at least one divider 110. The divider 110 is disposed in an inner portion of the container 102 and is adapted to divide the container 102 into a first compartment 112 disposed on a first side of the divider 110 and a second compartment 114 disposed on a second side of the divider 110 that is opposite the first side of the divider 110. While only a divider 110 is described herein, the principles of the present disclosure apply to a container 102 having any suitable number of dividers 110. Further, the principles of the present disclosure apply to a container 102 having additional or fewer compartments than described herein. The divider 110 is adapted to isolate fluid in the first compartment 112 from fluid in the second compartment 114, such that, the fluid in the first compartment 112 does not mix and/or interact with the fluid in the second compartment 114.

In some embodiments, the first compartment 112 is adapted to retain a first fluid. For example, as described above, the container 102 includes one or more openings and/or ports adapted to receive one or more fluids. In some embodiments, a first opening and/or port may correspond to the first compartment 112. For example, the first opening and/or port is adapted to receive the first fluid and direct the first fluid to the first compartment 112. The second compartment 114 is adapted to retain a second fluid. For example, a second opening and/or port may correspond to the second compartment 114. For example, the second opening and/or port is adapted to receive the second fluid and direct the second fluid to the second compartment 114.

In some embodiments, the first fluid is a different fluid than the second fluid. The first fluid includes a fluid capable of chemically interacting with the second fluid to form a charged compound. For example, the first fluid includes zinc chloride ($ZnCl_2$) and the second fluid includes sodium chlorite ($NaClO_2$). It should be understood that the first fluid and the second fluid are interchangeable. For example, the first fluid may include sodium chlorite and the second fluid may include zinc chloride. In some embodiments, the first fluid includes silver chloride (AgCl) and the second fluid includes sodium chlorite ($NaClO_2$). In some embodiments, the first fluid includes copper chloride ($CuCl_2$) and the second fluid includes sodium chlorite ($NaClO_2$). Additionally, or alternatively, the container 102 may include one or more additional fluid compartments. The one or more additional fluid compartments may be adapted to retain one or more additional fluids. For example, the one or more additional fluids may include antibacterial fluids, vitamin fluids, other suitable fluids, or a combination thereof. In some embodiments, the vitamin fluids may include vitamin A fluid, vitamin C fluid, vitamin D fluid, vitamin E fluid, other suitable vitamin fluids, or a combination thereof. In some embodiments, the first fluid and/or the second fluid may be infused with one or more antibiotics, one or more vitamins, or a combination thereof.

A ratio of the first fluid to the second fluid may vary based on the application and/or use of resulting charged compound and/or various characteristics of the first fluid and the second fluid may be altered and/or controlled, such that, a desired charged compound results from the interaction between the first fluid and the second fluid. Such ratios and/or characteristics are described in U.S. Pat. No. 6,409,992, which is incorporated by reference herein.

As described above, when the first fluid and the second fluid form a charged compound when the first fluid and the second fluid interact with one another. The system 100 includes a fluid charging portion 118. The fluid charging portion 118 is disposed at or near a lower portion 120 of the container 102. The second or lower portion 120 is disposed on an opposite side of the container 102 from the upper portion 108.

In some embodiments, one or more fluid transfer portions 122 extend from the lower portion 120 to the fluid charging portion 118. For example, a first fluid transfer portion 122A extends from the lower portion 120 to the fluid charging portion 118 and a second fluid transfer portion 122B extends from the lower portion 120 to the fluid charging portion 118. The first fluid transfer portion 122A is in communication with the first compartment 112 and the second fluid transfer portion 122B is in communication with the second compartment 114. While only a first and second transfer portions 122A and 122B are described herein, the system 100 may include any suitable number of transfer portions 122 in communication with corresponding compartments of the container 102.

In some embodiments, a portion of the first fluid transfers from the first compartment 112 to the fluid charging portion 118 via the first fluid transfer portion 122A and a portion of the second fluid transfers from the second compartment 114 to the fluid charging portion 118 via the second fluid transfer portion 122B. For example, each fluid transfer portion 122 may include a valve 124, as is generally illustrated in FIG. 2. The valves 124 are adapted to release fluid from the container 102 into the fluid charging portion 118. For example, each valve 124 may include a shutoff valve that is selectively opened to allow fluid to transfer from the container 102 to the fluid charging portion 118. In some embodiments, a medical professional operating the system 100 may actuate a control, such as a lever or a knob, associated with a valve 124 in order to allow fluid to transfer from the container 102 to the fluid charging portion 118. Conversely, the medical professional may actuate the control to prevent fluid from transferring from the container 102 to the fluid charging portion 118.

In some embodiments, fluid transfers from the container 102 to the fluid charging portion 118 due to the force of gravity acting on the fluid. The container 102 may be disposed at a position above the fluid charging portion 118. For example, the container 102 may be hung on an intravenous stand or other suitable stand. In some embodiments, the medical professional may hold the container 102 above the fluid charging portion 118 in order to allow gravity to act on fluid within the container 102.

In some embodiments, a pump, such as a pump 126, as is generally illustrated in FIG. 2, may promote transfer of fluid from the container 102 to the fluid charging portion 118. For example, the pump 126 may be in communication with the container 102 or other suitable component of the system 100. The pump 126 may create a current and/or force that promotes transferring the fluid from the container 102 to the fluid charging portion 118.

As described above, the portion of the first fluid transferred from the first compartment 112 interacts with the portion of the second fluid from the second compartment 114 to form a charged compound when the portion of the first fluid and the portion of the second fluid are in the fluid charging portion 118. In some embodiments, the charged compound transfers from the fluid charging portion 118 to a compound delivery portion 128 that extends from a first end of the compound delivery portion 128 from the fluid charging portion 118.

In some embodiments, the compound delivery portion 128 includes a flexible polymer tube or hose, a corrugated tube or hose, and/or other suitable tube or hose. The compound delivery portion 128 includes a generally circular profile having a diameter and a length. In some embodiments, the diameter and length may allow the charged compound to flow the compound delivery portion 128 at a predetermined rate. For example, a larger diameter may allow the charged compound to flow through the compound delivery portion 128 at a faster rate than a smaller diameter. Additionally, or alternatively, a longer length may allow the charged compound to flow through the compound delivery portion 128 at a slower rate than a shorter length.

In some embodiments, a control 130, as is generally illustrated in FIG. 2, may be disposed on the compound delivery portion 128 at or near the fluid charging portion 118. The control 130 may include features similar to those of the valves 124 described above. The medical professional operating the system 100 may actuate the control to allow the charged compound to transfer from the fluid charging portion 118 to the compound delivery portion 128.

In some embodiments, the charged compound is drawn into the compound delivery portion 128 as a result of the force of gravity acting on the charged compound and/or as a result of the pump 126 promoting the charged compound through the compound delivery portion 128. In some embodiments, a second end of the compound delivery portion 128 is adapted to connect to, couple to, attach to, and/or be in communication with the irrigation sleeve 104.

For example, the irrigation sleeve 104 includes a first aperture 132 disposed near an upper portion 134 of the irrigation sleeve 104. In some embodiments, the second end of the compound delivery portion 128 is adapted to be inserted into the first aperture 132. In some embodiments, the first aperture 132 may include a port adapted to receive the second end of the compound delivery portion 128. Additionally, or alternatively, the second end of the compound delivery portion 128 may be adapted to connect to, couple to, attach to, and/or be in communication with the first aperture 132 in other suitable manners than those described herein.

As described above, the charged compound transfers from the fluid charging portion 118 to the compound delivery portion 128. The charged compound exits the compound delivery portion 128 at the second end of the compound delivery portion 128 and enters the irrigation sleeve 104 at the first aperture 132. In some embodiments, and as is generally illustrated in FIG. 2, the first aperture 132 may include a filter 136. The filter 136 may include a screen or other suitable filter and is adapted to filter particulates from the charged compound before the charged compound irrigates the wound area and/or the patient's skin.

In some embodiments, the irrigation sleeve 104 a profile. The profile may include a profile corresponding to a portion of the patient's anatomy. For example, and as is generally illustrated in FIGS. 1 and 2, the profile may include a profile corresponding to a patient's foot. The irrigation sleeve 104 may include a generic profile, such that, the profile may accommodate various patients. In some embodiments, the profile may be adapted to match a particular patient. For example, the irrigation sleeve 104 may include a profile that corresponds to a patient's foot. The patient's foot may be measured and/or examined. The irrigation sleeve 104 may be manufactured to match the measurements and/or examination of the patient's foot.

In some embodiments, the profile may include a generic shape such as a cylinder. The irrigation sleeve 104 having a profile that includes a generic shape may be wrapped around a portion of the patient's anatomy, such as an arm or a leg. In some embodiments, the irrigation sleeve 104 may include an attachment portion (not shown). For example, a portion of the irrigation sleeve 104 may be opened to receive the corresponding portion of the patient's anatomy. The irrigation sleeve 104 may include closing mechanism adapted to close the irrigation sleeve 104 around the corresponding portion of the patient's anatomy. The closing mechanism may include a strap, tape, hook-and-loop fasteners, or other suitable closing mechanism. In some embodiments, irrigation sleeve 104 may be slid over the corresponding portion of the patient's anatomy. For example, the irrigation sleeve 104 generally illustrated in FIGS. 1 and 2 may be slid onto a patient's foot like a sock. In some embodiments, the irrigation sleeve 104 may include tightening features. For example, the irrigation sleeve 104 may include laces, straps, or other features that tighten and/or compress the irrigation sleeve 104 onto the patient.

In some embodiments, the irrigation sleeve 104 may include one or more fluid seals. The fluid seals may be disposed at one or more openings of the irrigation sleeve 104 in order to prevent fluid, such as the charged compound, from exiting the irrigation sleeve 104 at the one or more openings. In some embodiments, the irrigation sleeve 104 may include a fluid seal disposed around the upper portion 134, such that, when the irrigation sleeve 104 is on the patient, a fluid tight seal is formed at the upper portion 134.

In some embodiments, the irrigation sleeve 104 covers one or more wound areas on the patient. By way of non-limiting example only, the irrigation sleeve 104 may be adapted to cover one or more diabetic foot ulcers. While only limited examples are described herein, the irrigation sleeve 104 may be adapted to cover any suitable wound area or portion of the patient's skin. As the charged compound enters the irrigation sleeve 104 through the first aperture 132, the charged compound is directed to the one or more wound areas. The charged compound irrigates the one or more wound areas and/or the patient's skin in order to promote higher levels of $E_h$ in the one or more wound areas, which decreases metabolism and/or growth of anaerobic bacteria in the one or more wound areas. By decreasing metabolism and/or growth of anaerobic bacteria in the one or more wound areas, infections in the one or more wound areas may be prevented and/or cured. Colonization may also be decreased, thereby increasing the wound healing potential in the area.

As described above, the charge of the charged compound decreases over a period. As the charge of the charged compound decreases below a charge threshold, the charged compound is converted into a residual compound. The residual compound may be ineffective to promote higher levels of $E_h$ in the one or more wound areas. In order to prevent the residual compound from irrigating the one or more wound areas, the control 130 may include a timer. The timer may act as a visual guide for the medical professional to determine when the charged compound has lost or started to lose its charge. The medical professional may stop irrigating the wound area and/or patient's skin based on the timer. In some embodiments, the timer may include a countdown time. For example, the timer may be started when charged compound is released from the fluid charging portion 118. The timer may be set to an amount of time that the charged compound will retain enough free available ions to effectively increase $E_h$ in the one or more wound areas. The medical professional may stop irrigating the one or more wound areas and/or patient's skin when the timer reaches zero. While only limited examples are described herein, the timer may include any suitable timer.

In some embodiments, the residual compound may be released from the irrigation sleeve 104. In some embodiments, the irrigation sleeve 104 includes a second aperture 138. The second aperture 138 may be disposed at a lower portion 140 of the irrigation sleeve 104. The lower portion 140 is disposed on the irrigation sleeve 104 opposite the upper portion 134. In some embodiments, a valve may be disposed at or near the second aperture 138. The medical professional may actuate the valve to create a vacuum effect within the irrigation sleeve 104. The vacuum effect may act to draw the residual compound toward the second aperture 138. In some embodiments, the force of gravity acting on the residual compound may act to draw the residual compound toward the second aperture 138. The residual compound may exit the irrigation sleeve 104 through the second aperture 138. In some embodiments, a filter 142 may be disposed at or near the second aperture 138. The filter 142 includes features similar to the filter 136.

In some embodiments, a drain portion 144 is connected to, coupled to, attached to, or in communication with the second aperture 138 at a first end of the drain portion 144. The drain portion 144 may include a tube or hose and includes features similar to those of the compound delivery portion 128. The drain portion 144 extends from the second aperture 138 from the first end of the drain portion 144 to a second end of the drain portion 144. The second end of the drain portion 144 may be connected to, coupled to, attached to, or in communication with the reservoir 106.

The reservoir 106 may include canister having a generally cylindrical profile. In some embodiments, the reservoir 106 may include a canister having a profile other than cylindrical, a bag, a receptacle, or other suitable reservoir. The reservoir 106 is adapted to receive the residual compound through the drain portion 144. In some embodiments, the reservoir 106 may receive residual compound from a plurality of irrigation sleeves 104. The residual compound within the reservoir 106 may be disposed of after the residual compound is received by the reservoir 106.

Figure 3:
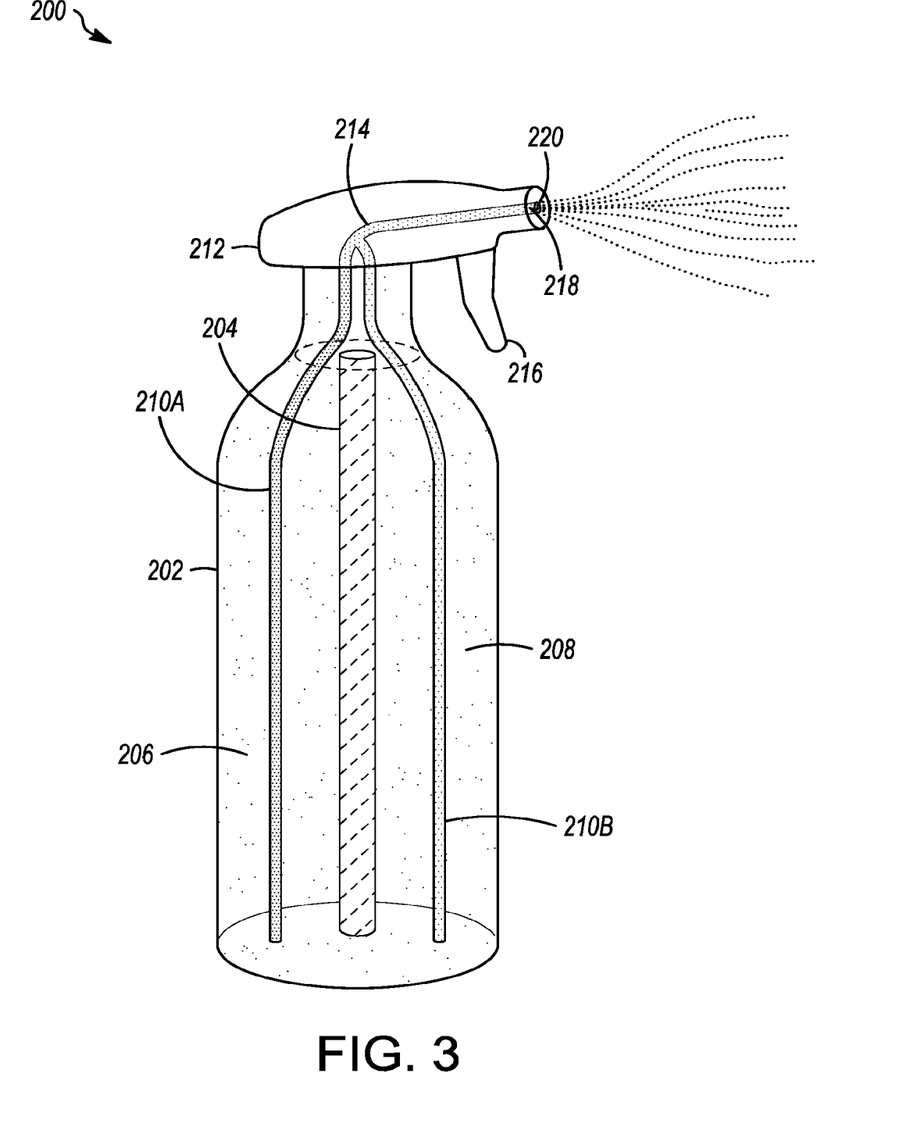
FIG. 3 generally illustrates an alternative wound and/or skin irrigation system according to the principles of the present disclosure.

FIG. 3 generally illustrates an alternative wound and/or skin irrigation system 200 according to the principles of the present disclosure. In some embodiments, a medical professional may irrigate surgical wounds during (operative wounds) and/or after (postoperative wounds) a patient surgery. The medical professional may operate the system 200 to direct charged compound to the operative and/or postoperative wounds to raise $E_h$ in the wounds in order to prevent and/or cure operative and/or postoperative infections in the wounds. The system 200 may include a portable or substantially portable irrigation system that includes a container 202. The container 202 may include a generally cylindrical profile or other suitable profile. The container 202 is adapted to receive one or more fluids and includes features similar to those of the container 102. In some embodiments, the container 202 includes a divider 204. The divider 204 includes features similar to the divider 110. The divider 204 defines a first compartment 206 disposed on a first side of the divider 204 and a second compartment 208 disposed on a second side of the divider 204. The second side of the divider 204 is disposed opposite the first side of the divider 204.

The first compartment 206 includes features similar to those of the first compartment 112 and the second compartment 208 includes features similar to those of the second compartment 114. The first compartment 206 is adapted to receive and retain a first fluid. The first fluid includes features similar to the first fluid described above with respect to FIGS. 1 and 2. The second compartment 208 is adapted to receive and retain a second fluid. The second fluid includes features similar to the second fluid described above with the respect to FIGS. 1 and 2. While only a first compartment 206 and a second compartment 208 is described herein, the system 200 may include any suitable number of compartments and may receive and retain any suitable number of fluids.

The system 200 includes one or more fluid transfer portion 210. For example, the system 200 includes a first fluid transfer portion 210A disposed in the first compartment 206 and a second fluid transfer portion 210B disposed in the second compartment 208. The first fluid transfer portion 210A is adapted to allow a portion of the first fluid to be drawn out of the first compartment 206 and the second fluid transfer portion 210B is adapted to allow a portion of the second fluid to be drawn out of the second compartment 208.

In some embodiments, the system 200 includes an irrigator 212 disposed at or near an upper portion of the container 202. The irrigator 212 is adapted to apply charged compound to a surgical wound. For example, the irrigator 212 includes a fluid charging portion 214 disposed in an interior portion of the irrigator 212. The fluid charging portion 214 includes features similar to the fluid charging portion 118. The fluid charging portion 214 is adapted to receive the portion of the first fluid and the portion of the second fluid. As described above with respect to the fluid charging portion 118, the portion of the first fluid and the portion of the second fluid interact to form a charged compound in the fluid charging portion 214.

In some embodiments, the irrigator 212 includes an actuator 216. The actuator 216 may include a trigger or other suitable actuator. When the medical professional actuates the actuator 216, a vacuum and/or suction effect is created within the container 202. The portion of the first fluid and the portion of the second fluid are drawn into the fluid charging portion 214 in response to the vacuum and/or suction effect.

The irrigator 212 includes a compound applicator 218. The compound applicator 218 is adapted to apply the charged compound to the surgical wound, expelling the charged compound from the fluid charging portion 214 in response to the vacuum and/or suction effect created by the actuator 216. The compound applicator 218 may include a selectively adjustable head 220. The head 220 may be adjusted to provide a wider or narrower compound application field. The medical professional may direct the charged compound to the surgical wound, aiming the irrigator 212 in a direction that applies the charged compound to the surgical wound when the actuator 216 is actuated by the medical professional.

Figure 4:
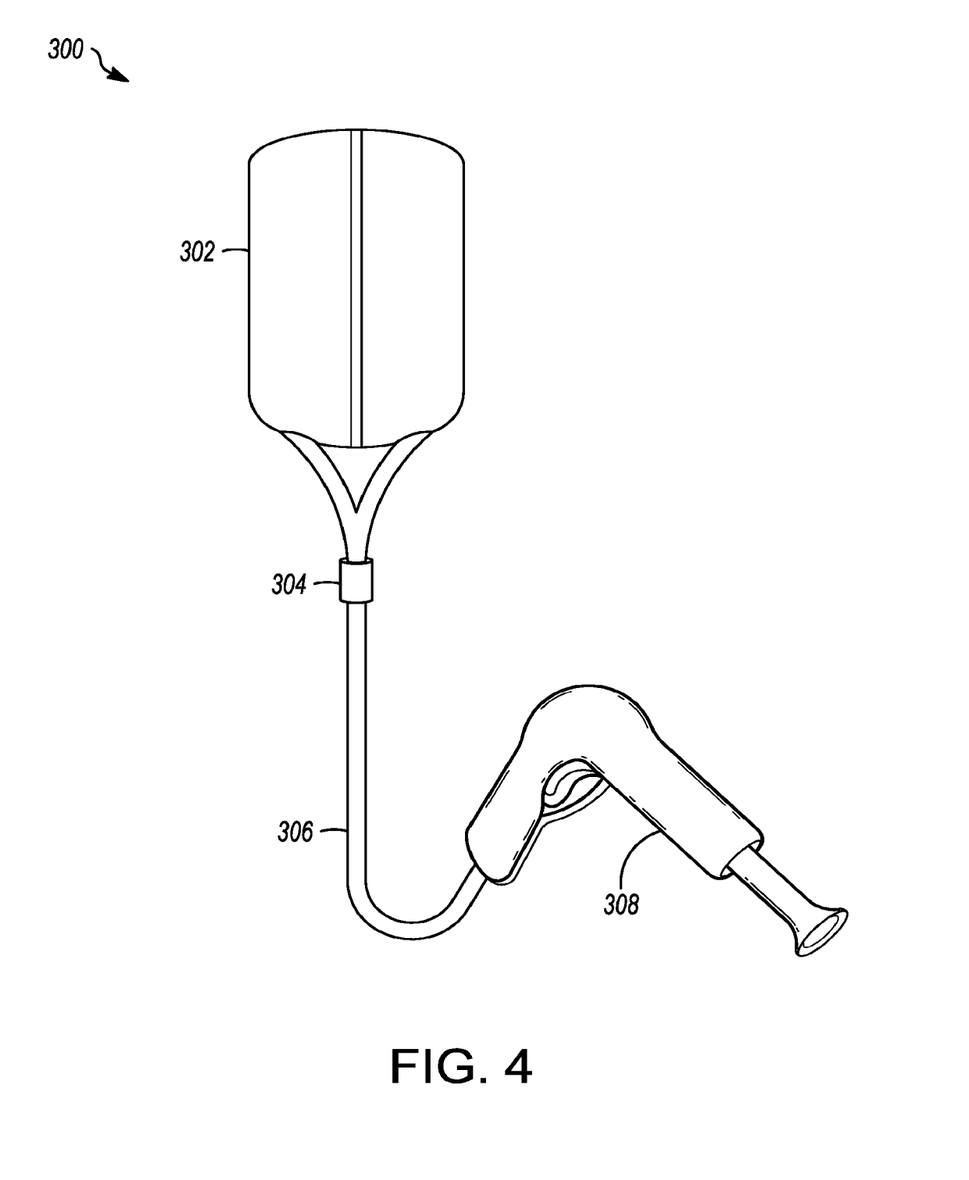
FIG. 4 generally illustrates an alternative wound and/or skin irrigation system according to the principles of the present disclosure.

FIG. 4 generally illustrates an alternative wound and/or skin irrigation system 300 according to the principles of the present disclosure. The medical professional may operate the system 300 to direct charged compound to the operative and/or postoperative wounds to raise $E_h$ in the wounds in order to prevent and/or cure operative and/or postoperative infections in the wounds. The system 300 may include a portable or substantially portable irrigation system that includes a container 302. The container 302 includes features similar to those of the container 102 described with respect to FIGS. 1 and 2. The system 300 includes a fluid charging portion 304. The fluid charging portion 304 includes features similar to those of the fluid charging portion 118 described with respect to FIGS. 1 and 2. The system includes a compound delivery portion 306. The compound delivery portion 306 includes features similar to those the compound delivery portion 128 described with respect to FIGS. 1 and 2.

In some embodiments, the system 300 includes an irrigator 308. The irrigator 308 may include features similar to those of the irrigator 212 described with respect to FIG. 3. In some embodiments, the irrigator 308 includes a continuously or substantially continuously irrigating irrigator. For example, the irrigator 308 may include a powered and/or motorized irrigator adapted to continuously or substantially continuously apply charged compound to a surgical wound. The medical professional may actuate an actuator associated with the irrigator 308. While the actuator is actuated, the irrigator 308 may continuously or substantially continuously apply charged compound to a surgical wound that the medical professional is aiming and/or directing the irrigator 308 toward.

Figure 5:
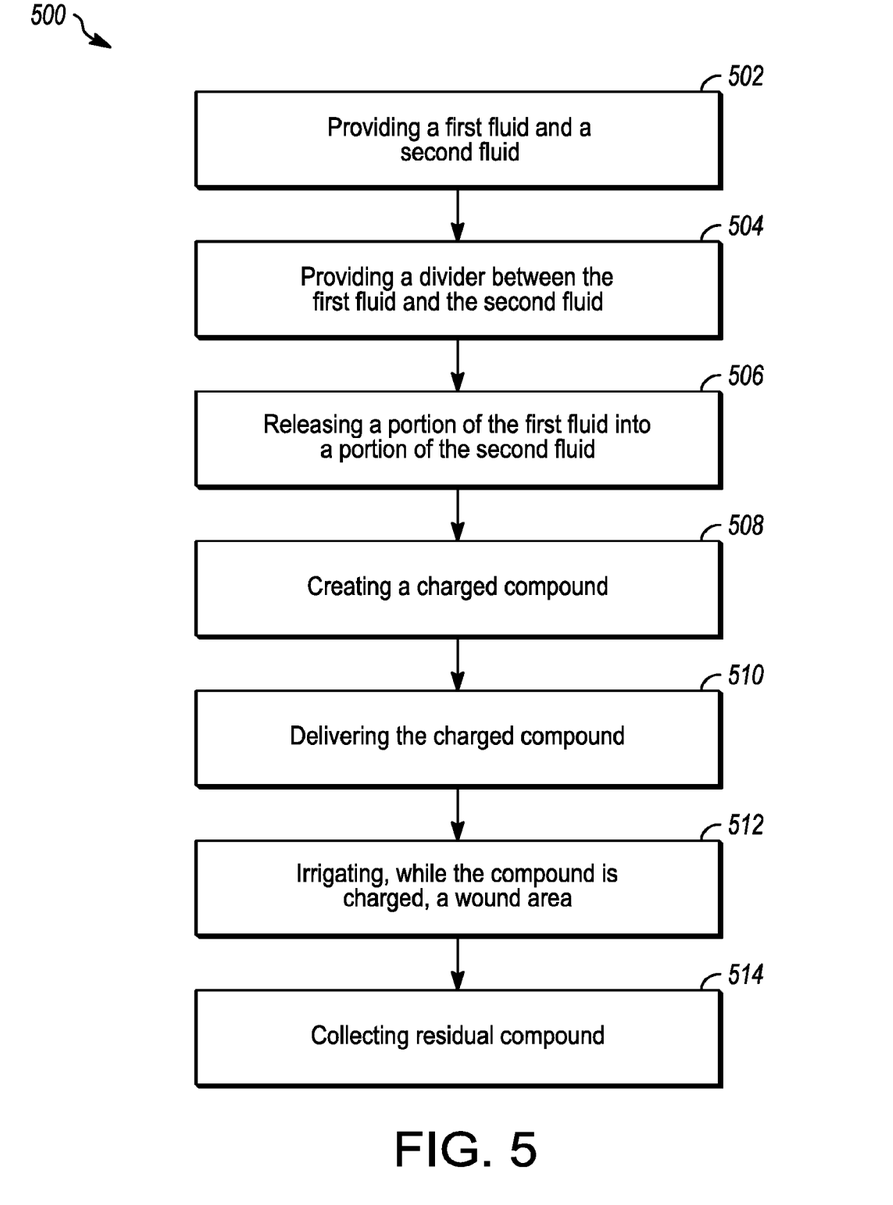
FIG. 5 is a flow diagram illustrating a wound and/or skin irrigation method according to the principles of the present disclosure.

FIG. 5 is a flowchart generally illustrating a wound and/or skin irrigation method 500 according to the principles of the present disclosure. At 502, the method 500 includes providing a first fluid and a second fluid. For example, as described above, the first fluid and the second fluid may be provided in a first compartment and a second compartment respectively. At 504, the method 500 includes providing a divider between the first fluid and the second fluid. For example, the divider may be provided to separate the first fluid from the second fluid, such that, the first fluid does not interact with the second fluid.

At 506, the method 500 includes releasing a portion of the first fluid and a portion of the second fluid. For example, the portion of the first fluid and the portion of the second fluid may be released to a fluid charging portion, such as the fluid charging portion 118, the fluid charging portion 214, or the fluid charging portion 304. At 508, the method 500 includes creating a charged compound. For example, the portion of the first fluid interacts with the portion of the second fluid to form a charged compound, as described above. At 510, the method 500 includes delivering the charged compound. For example, as described above, the charged compound may be delivered to the irrigation sleeve 104, the irrigator 212, or the irrigator 308.

At 512, the method 500 includes irrigating, while the compound is charged, a wound area. For example, as described above, a medical professional irrigates one or more wound areas, one or more operative and/or postoperative wounds, a portion of a patient's skin, or a combination thereof using the charged compound while the charged compound is charged. At 514, the method 500 collects residual compound. For example, as described above, as the charge of the charged compound decreases below the charge threshold, the charge compound becomes a residual compound. The residual compound may be collected by the reservoir 106. In some embodiments, the method 500 may omit 514.

As used herein, the terminology "or" is intended to mean an inclusive "or" rather than an exclusive "or". That is, unless specified otherwise, or clear from context, "X includes A or B" is intended to indicate any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form.

Further, for simplicity of explanation, although the figures and descriptions herein may include sequences or series of steps or stages, elements of the methods disclosed herein may occur in various orders or concurrently. Additionally, elements of the methods disclosed herein may occur with other elements not explicitly presented and described herein. Furthermore, not all elements of the methods described herein may be required to implement a method in accordance with this disclosure. Although aspects, features, and elements are described herein in particular combinations, each aspect, feature, or element may be used independently or in various combinations with or without other aspects, features, and elements.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for irrigating a surgical wound, the method comprising:
   retaining a first fluid on a first side of a divider;
   retaining a second fluid on a second side of a divider, the second side of the divider being disposed opposite the first side of the divider;
   drawing a portion of the first fluid and a portion of the second fluid into a fluid charging portion such that the first and second fluid portions react to form a charged compound;
   and irrigating the surgical wound with the charged compound.

2. The method of claim 1, further comprising preventing delivery of the charged compound to the surgical wound once a charge of the charged compound decreases below a charge threshold.

3. The method of claim 1, further comprising controlling flow of the charged compound from the fluid charging portion to the surgical wound with at least one control flow valve.

4. The method of claim 1, wherein the surgical wound includes an operative wound.

5. The method of claim 1, wherein the surgical wound includes a postoperative wound.

6. The method of claim 1, further comprising applying the charged compound to the surgical wound continuously.

7. The method of claim 1, wherein the charged compound includes a zinc compound that includes at least some free available zinc ions.

8. The method of claim 1, wherein the charged compound includes at least one $E_h$ raising component.

* * * * *